US00PP16700P2

(12) United States Plant Patent
Robb

(10) Patent No.: US PP16,700 P2
(45) Date of Patent: Jun. 20, 2006

(54) LAVENDER PLANT NAMED 'BELROU'

(50) Latin Name: *Lavandula stoechas*
Varietal Denomination: Belrou

(76) Inventor: John Robb, RMB 2117 Greta Road, Kulnurra NSW 2250 (AU)

( * ) Notice: Subject to any disclaimer, the term of this patent is extended or adjusted under 35 U.S.C. 154(b) by 47 days.

(21) Appl. No.: 11/113,393

(22) Filed: Apr. 23, 2005

(51) Int. Cl.
*A01H 5/00* (2006.01)

(52) U.S. Cl. ..... Plt./226
(58) Field of Classification Search ..... Plt./226
See application file for complete search history.

(56) References Cited

U.S. PATENT DOCUMENTS

PP15,207 P2 * 10/2004 McNaughton ..... Plt./226

* cited by examiner

*Primary Examiner*—Kent Bell
*Assistant Examiner*—W. C. Haas
(74) *Attorney, Agent, or Firm*—C. A. Whealy

(57) ABSTRACT

A new and distinct cultivar of Lavender plant named 'Belrou', characterized by its upright, somewhat outwardly spreading and mounded plant habit; freely branching habit, dense and bushy plant form; vigorous growth habit; and violet-colored flowers with light pink-colored terminal flower bracts.

1 Drawing Sheet

Botanical designation: *Lavandula stoechas.*
Cultivar denomination: 'Belrou'.

CROSS-REFERENCE TO RELATED APPLICATIONS

The present application is co-pending with the following related application: U.S. Plant patent application Ser. No. 11/113,372, Lavender Plant Named 'Belros'.

BACKGROUND OF THE INVENTION

The present Invention relates to a new and distinct cultivar of Lavender plant, botanically known as *Lavandula stoechas,* and hereinafter referred to by the name 'Belrou'.

The new Lavender is a product of a planned breeding program conducted by the Inventor in Kulnura, New South Wales, Australia. The objective of the breeding program was to create new compact and freely branching Lavender cultivars with large and attractive flowers and good garden performance.

The new Lavender originated from an open-pollination in 1999 of a proprietary selection of *Lavandula stoechas* identified as code number 00-38, not patented, as the female, or seed, parent with an unknown selection of *Lavandula stoechas,* as the male, or pollen, parent. The new Lavender was discovered and selected by the Inventor as a single flowering plant within the progeny of the stated open-pollination grown in a controlled environment in Kulnura, New South Wales, Australia in September, 2000.

Asexual reproduction of the new cultivar by terminal cuttings at Kulnura, New South Wales, Australia, since 2000, has shown that the unique features of this new Lavender are stable and reproduced true to type in successive generations.

SUMMARY OF THE INVENTION

Plants of the cultivar 'Belrou' have not been observed under all possible environmental conditions. The phenotype may vary somewhat with variations in environment such as temperature and light intensity without, however, any variance in genotype.

The following traits have been repeatedly observed and are determined to be the unique characteristics of 'Belrou'. These characteristics in combination distinguish 'Belrou' as a new and distinct cultivar:

1. Upright, somewhat outwardly spreading and mounded plant habit.
2. Freely branching habit, dense and bushy plant form.
3. Vigorous growth habit.
4. Violet-colored flowers with light pink-colored terminal flower bracts.

Plants of the new Lavender differ from plants of the female parent selection in the following characteristics:

1. Plants of the new Lavender and the female parent selection differ in flower coloration.
2. Plants of the new Lavender and the female parent selection differ in flower bract coloration.

Plants of the new Lavender differ primarily from plants of the cultivar 'Belros', disclosed in U.S. Plant patent application Ser. No. 11/113,372, in flower and terminal flower bract coloration.

Plants of the new Lavender can be compared to plants of the Lavender cultivar Kew Red, not patented. In side-by-side comparisons conducted in Kulnura, New South Wales, Australia, plants of the new Lavender differed from plants of the cultivar Kew Red in the following characteristics:

1. Plants of the new Lavender were taller and more uniform in growth habit than plants of the cultivar Kew Red.
2. Plants of the new Lavender had longer leaves than plants of the cultivar Kew Red.

3. Plants of the new Lavender had larger terminal flower bracts than plants of the cultivar Kew Red.
4. Plants of the new Lavender and the cultivar Kew Red differed in terminal flower bract coloration as plants of the cultivar Kew Red had light lavender-colored terminal flower bracts.
5. Plants of the new Lavender had longer peduncles than plants of the cultivar Kew Red.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new Lavender.

The photograph at the top of the sheet comprises a side perspective view of a typical flowering plant of 'Belrou' grown in a container.

The photograph at the bottom of the sheet comprises a close-up view of typical inflorescences of 'Belrou'.

DETAILED BOTANICAL DESCRIPTION

In the following description, color references are made to The Royal Horticultural Society Colour Chart, 1999 Edition, except where general terms of ordinary dictionary significance are used. Plants used for the aforementioned photographs and following description were grown under conditions which closely approximate commercial production conditions during the spring in a glass-covered greenhouse in Kulnura, New South Wales, Australia for about four to six months in 15-cm containers.

Botanical classification: *Lavandula stoechas* cultivar 'Belrou'.

Parentage:

*Female, or seed, parent.*—Proprietary selection of *Lavandula stoechas* identified as code number 00-38, not patented.

*Male, or pollen, parent.*—Unknown selection of *Lavandula stoechas,* not patented.

Propagation:

*Type cutting.*—Terminal vegetative cuttings.

*Time to initiate roots.*—About 10 to 14 days at 18° C. to 21° C.

*Root description.*—Fine, fibrous.

*Rooting habit.*—Freely branching.

Plant description:

*Form.*—Perennial plant; upright, somewhat outwardly spreading and mounded plant form. Freely branching habit with lateral branches potentially at every node; dense and bushy plant habit; vigorous growth habit. Flowers in verticillasters on crowded spikes with showy terminal flower bracts.

*Plant height.*—About 50 cm.

*Plant width.*—About 50 cm.

*Foliage description.*—Arrangement: Opposite, simple; decurrent. Length: About 3 cm. Width: About 4 mm. Shape: Linear. Apex: Mucronate. Base: Cuneate. Margin: Entire; edges, recurved. Texture, upper surface: Fine pubescence. Texture, lower surface: Smooth. Fragrance: Very aromatic, pungent. Venation pattern: Pinnate; reticulate. Color: Developing foliage, upper and lower surfaces: 137A. Fully expanded foliage, upper and lower surfaces: 137C; venation, 134A.

Flower description:

*Flower arrangement and shape.*—Small single flowers in compact verticillasters on crowded spikes. Freely flowering, about five to six rows of flowers and flower buds per spike; flowers tubular with five lobes; inflorescences with showy terminal bracts.

*Natural flowering season.*—Continuous throughout the Spring.

*Flower longevity on the plant.*—Individual inflorescences last about two weeks on the plant and individual flowers last about two to four days on the plant. Flowers, not persistent; terminal flower bracts, persistent.

*Inflorescence size.*—Height: About 3 cm. Diameter: About 1.3 cm.

*Flowers.*—Diameter: About 2 mm. Depth (height): About 4 mm.

*Petals.*—Arrangement: Five, fused into a tube. Length, lobes: About 1 mm. Width, lobes: About 1 mm. Shape: Roughly spatulate. Apex: Rounded. Margin: Entire. Texture, upper and lower surfaces: Smooth, glabrous; velvety. Color: When opening, upper and lower surfaces: 87B. Fully opened, upper and lower surfaces: 87B.

*Terminal flower bracts.*—Arrangement: About four in a single whorl at inflorescence apex. Length: About 1.4 cm. Width: About 8 mm. Shape: Oblong. Apex: Obtuse. Base: Obtuse. Margin: Entire. Texture, upper and lower surfaces: Smooth, glabrous; velvety. Color, immature, upper and lower surfaces: 69D; venation, close to 87A. Color, immature, upper and lower surfaces: 69D; venation, close to 87A.

*Peduncle.*—Strength: Moderately strong. Length: About 4 cm. Diameter: About 2 mm. Aspect: Mostly upright. Color: Close to 134A.

*Reproductive organs.*—Stamens: Quantity per flower: Four. Anther shape: Oval. Anther length: Less than 1 mm. Anther color: Close to 14A. Pollen amount: Scarce. Pollen color: Close to 14A. Pistils: Quantity per flower: One. Stigma shape: Rounded. Stigma color: Close to 157A. Style color: Close to 157D.

*Seed/fruit.*—Seed and fruit production has not been observed.

Disease/pest resistance: Plants of the new Lavender have not been noted to be resistant to pathogens and pests common to Lavender.

Weather tolerance: Plants of the new Lavender have exhibited good tolerance to rain and wind and have been observed to tolerate temperatures from −2° C. to 40° C.

It is claimed:

1. A new and distinct cultivar of Lavender plant named 'Belrou', as illustrated and described.

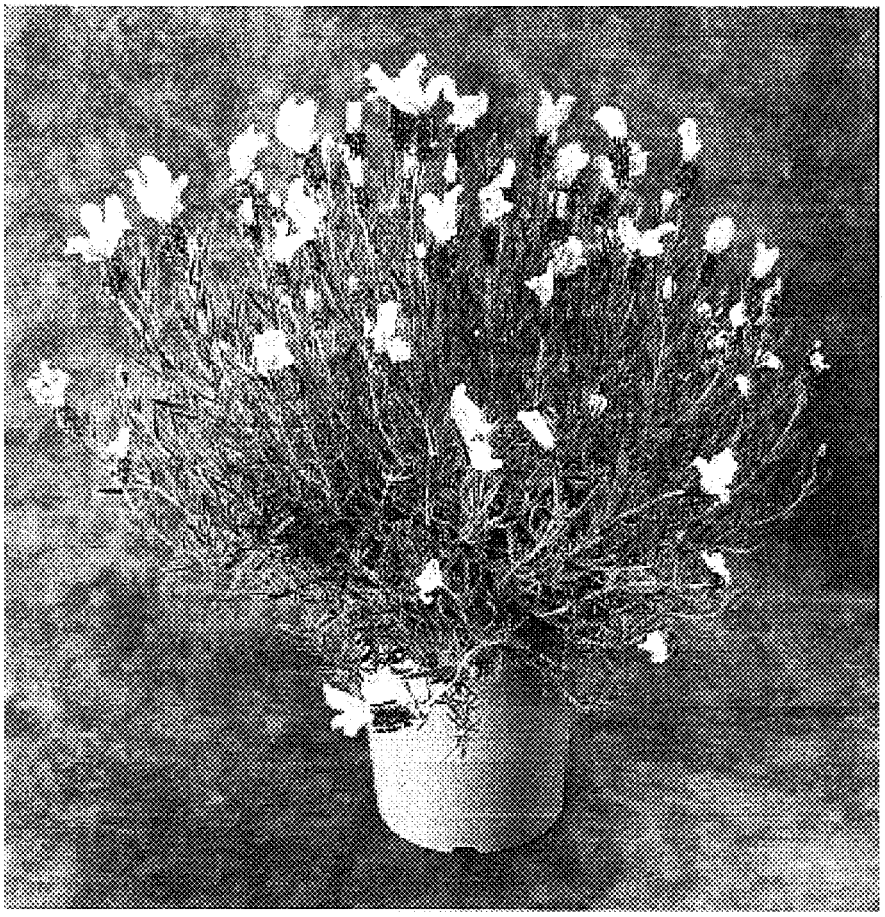
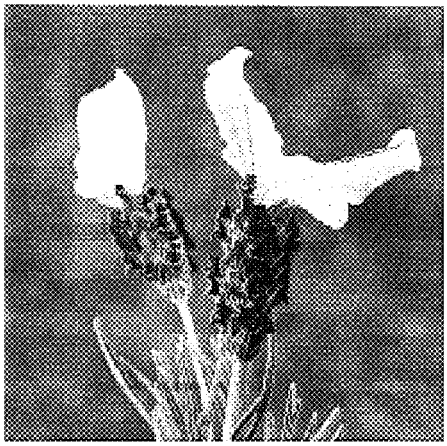

* * * * *